(12) United States Patent
Rey et al.

(10) Patent No.: US 6,686,189 B2
(45) Date of Patent: Feb. 3, 2004

(54) POLYPEPTIDES HAVING LIPASE ACTIVITY AND NUCLEIC ACIDS ENCODING SAME

(75) Inventors: Michael W. Rey, Davis, CA (US); Elizabeth J. Golightly, Davis, CA (US)

(73) Assignee: Novozymes Biotech, Inc., Davis, CA (US)

( * ) Notice: Subject to any disclaimer, the term of this patent is extended or adjusted under 35 U.S.C. 154(b) by 19 days.

(21) Appl. No.: 10/171,229

(22) Filed: Jun. 12, 2002

(65) Prior Publication Data

US 2003/0040450 A1 Feb. 27, 2003

Related U.S. Application Data

(62) Division of application No. 09/703,416, filed on Oct. 31, 2000, now Pat. No. 6,432,898.

(51) Int. Cl.[7] .............................. C12N 9/16; C12N 1/20; C12N 15/00; C07H 21/04

(52) U.S. Cl. ................. 435/196; 435/252.3; 435/320.1; 435/929; 536/23.2

(58) Field of Search .............................. 435/196, 252.3, 435/320.1, 929; 536/23.2

(56) References Cited

FOREIGN PATENT DOCUMENTS

| | | |
|---|---|---|
| EP | 0869167 | 12/1997 |
| WO | WO 98/26057 | 6/1998 |

*Primary Examiner*—Tekchand Saidha
(74) *Attorney, Agent, or Firm*—Robert L. Starnes

(57) ABSTRACT

The present invention relates to isolated polypeptides having lipase activity and isolated nucleic acid sequences encoding the polypeptides. The invention also relates to nucleic acid constructs, vectors, and host cells comprising the nucleic acid sequences as well as methods for producing and using the polypeptides.

15 Claims, 4 Drawing Sheets

Fig. 1A

```
GCAAGGCGAACCCTTCGTTCAAGGTCGTTGCCACAGGTCACTCGTTGGGTGGTGTAGCTACACTAGC  2030
 R  K  A  N  P  S  F  K  V  V  A  T  G  H  S  L  G  G  A  V  A  T  L  A
AGGTGCGAACCTGCGAGTTGGTGGTACGCCAGTTGACATCTACACGGCTCACCCCGAGTTGGAAAC    2100
 G  A  N  L  R  V  G  G  T  P  V  D  I  Y  T  Y  G  S  P  R  V  G  N
ACGCAACTCGCTGCCTTCATCTCTAACCAGGCTGGTGGAGAGTTCCGCGTTACGAACGCCAAGGACCCCG 2170
 T  Q  L  A  A  F  I  S  N  Q  A  G  E  F  R  V  T  N  A  K  D  P
TGCCTCGTCCTCTGGTCTTTGGATACCGGCACACATCCCCGAGTACTGGTTGTCTGGTAGCGG       2240
 V  P  R  L  P  P  L  V  F  G  Y  R  H  T  S  P  E  Y  W  L  S  G  S  G
AGGTAACAAGGTTGACTACACCATCAATGATGTCAAGGTGTGTGAGGGTGCTGCCAACCTTCAGTGCAAC 2310
 G  N  K  V  D  Y  T  I  N  D  V  K  V  C  E  G  A  A  N  L  Q  C  N
GGTGGAACACTCGGATTGGATATCGACGCCCATCTCCACTACTTCCAGGAGACCGATGCTTGCTCTGGTT 2380
 G  G  T  L  G  L  D  I  D  A  H  L  H  Y  F  Q  E  T  D  A  C  S  G
CCGGTATCGCGTGGAGAAGATACAGGAGAGTCGTAAGCGTCGGAGAGCATCTCGGAGAGGCCACTATGACAGA 2450
 S  G  I  A  W  R  R  Y  R  S  A  K  R  E  S  I  S  E  R  A  T  M  T  D
TGCCGAGCTGGAGAAGCTTAACAACTATGTTGCGATGGATAAGGAGTATGTCAAGACTCACGCCAAC   2520
 A  E  L  E  K  L  N  N  Y  V  A  M  D  K  E  Y  V  K  T  H  A  N
CGCTCATCGTAGTATGACATTTACGCAGTAACGATATAATTACCATAACAAAACTCTGGATACCATTCT  2590
 R  S  S  .
GGTGCAAGCATGGCGAAGAAACATCATTATCTATGTGAATGTATCATAACTCCTTACGCCATGCCGT    2660
TGATCTTACTACTGAGACACGAACAAATACTCAGTCATGTACAACTCCAAAGCACCGAATGACTTCTGCT 2730
TTTTGGCAAAGCACCGAAACCAATCATTCAAACCCCCTCCACCTTCATGCACCCAAAGACATTGACTTCCCGGATA 2800
GAGAATGACACCACGAGGCACGCAGACCCCAGAACAAATCCGTCACTGCCTCACAGAAACTGATCTCCAATT 2870
TTAGGGCATGCTCGGAAAATGAACCCAGAACAAATCCGTCACTGCCTCACAGAAACTGATCTCCAATT    2940
```

Fig. 1B

SEQUENCE LISTING

<160> NUMBER OF SEQ ID NOS: 10

<210> SEQ ID NO 1
<211> LENGTH: 2940
<212> TYPE: DNA
<213> ORGANISM: Fusarium venenatum

<400> SEQUENCE: 1

```
aattcatgtg aatctactat gtaacagtat gttgtattgc attacccatc aacgttgaat      60
cgttgcgacg taacggcccg gttcaagcga gatgtagata tgttggtagt taattgatgg     120
gttaggtatt cttttcatca actcggtatt ctcattcccc agatatcggc acttgtcttt     180
actccagatt tcatatcgca tcgagttata tacagtccca attgagtcga ctaccccgtc     240
caaaacaggt tttctcacaa accaaccgca gcctaacaaa aagtcccttg tctttctgca     300
ataaatgctg acaccccctg gcttttagg actgacggct cacgatgcag ccgttgcgat      360
aattaattga caattacccg cacattgatg catacttggc ggtcaggtca ggtcaggctg     420
aagcatacct attgggtcat ttatttgccg atcgtggtga aaagaatgca agtgataact     480
agttacgagt cgctttatga aagatggttg gtcgaaactg tcaatatggc atgggcggca     540
aatcgtttgg tctcaactct atagcatgta ctataattgg tcttttcatc acagtcacgc     600
caaagtgcca gtctcagact atggaccaac cactttcctc cttcacgtct aaattgactt     660
gatcaccaga ctcgaatatt ttttctttc ttctataccc ctaggatcat acaatacgaa       720
ccccaactca actcgagaga gagagtcccc ttcccaacat tttgacagcc cttgctcttc     780
tcctcccagg atgtaacaga agctgaaagg gtaccctgt agcccacctt tacccaccat      840
cttttccatc tgtatcggtg catcccatca caaccctcac gtggtccgag atcgtcgtta     900
cccgtattgg aagctcactc cgggcccaac gagagattgg accaaggaaa aataactttg     960
agacctcttc aagcagtcgg tcattcgtta ctgggatgtg tagtcgataa tgcggggtga   1020
caggccctca atccagcacc caccatcatg ggcactgact gtactaccgg agcccatcat   1080
ttcgtttttg ggtcctggcg tctacttgac cgactgagtt tgccaagatg gatggcatga   1140
gagacagtgg ttaggctggg cgggtattgt gatgagagaa agcgagagac tagttagaag   1200
caaagaaaaa agatatataa gctgtcacat ccctcatgaa catgctgttc ttgtaagtcg   1260
ggatatcagg gccagcttca gtattcagta tcctttctga gggagttgca ccttgtcaca   1320
gcttgtctgt ctatcactta tacttaccct tggaccacgt tctttgtctg tcaagatgca   1380
tctcctatca ctcctctcaa ttgccaccct tgcggtagcc agccctctga gcgttgaaga   1440
ttacgccaag gctctcgatg aaagaggtaa aacgattctc tgttcccata acaattccaa   1500
tactcacaga cctagctgtt tctgtctcta ccaacgactt tggcaacttc aagttctaca   1560
tccagcacgg tgccgcagca tactgtaact ctgaagccgc agccggtgca aaggtcacct   1620
```

```
gcggaggaaa cggttgccca acggtccagt ccaatggtgc caccatcgtg gcatctttcc   1680
tgtaagtcta acatatcaca aacacatcat caactccaaa cttacaaatc tctttatagt   1740
ggctcaaaga ctggcatcgg tggctacgtc gcgaccgact ctgcacgcaa ggaaatcgtc   1800
ctctcggttc gcgtagcac caacattcgc aactggctta ccaacctcga cttcgaccag   1860
gatgactgca gcttgacctc cggctgtgga gtgcacggag gcttccagag agcctggaat   1920
gagatctcgg ccgcagcaac cgccgctgtc gcaaaggccc gcaaggcgaa cccttcgttc   1980
aaggtcgttg ccacaggtca ctcgttgggt ggtgctgtag ctacactagc aggtgcgaac   2040
ctgcgagttg gtggtacgcc agttgacatc tacacctacg gctcaccccg agttggaaac   2100
acgcaactcg ctgccttcat ctctaaccag gctggtggag agttccgcgt tacgaacgcc   2160
aaggaccccg tgcctcgtct ccccctctg gtctttggat accggcacac atcccccgag   2220
tactggttgt ctggtagcgg aggtaacaag gttgactaca ccatcaatga tgtcaaggtg   2280
tgtgagggtg ctgccaacct tcagtgcaac ggtggaacac tcggattgga tatcgacgcc   2340
catctccact acttccagga gaccgatgct tgctctggtt ccggtatcgc gtggagaaga   2400
tacaggagtg ctaagcgtga gagcatctcg gagagggcca ctatgacaga tgccgagctg   2460
gagaagaagc ttaacaacta tgttgcgatg gataaggagt atgtcaagac tcacgccaac   2520
cgctcatcgt agtatgacat ttacgcagta acgatataat taccataaca aaaactctgg   2580
ataccattct ggtgcaagca tggcgaagaa aacatcatta tctatgtgaa tgtatcataa   2640
ccatccttac gccatgccgt tgatcttact actgagacaa aatactcagt catgtacaac   2700
aaactccaaa gcaccgaatg acttctggct ttttggcaaa gcacgaaacc aatcattcaa   2760 accccctccac gaccatgccc tgcgcattgg gaacacccac gagaatgaca ccacgaggca   2820
cgcggacact cttcaccttc atgcacccaa agacattgac ttcccggata ttagggcatg   2880
ctcggaaaat ggaacccaga acaaaatccg tcactgcctc acagaaactg atctccaatt   2940
```

<210> SEQ ID NO 2
<211> LENGTH: 349
<212> TYPE: PRT
<213> ORGANISM: Fusarium venenatum

<400> SEQUENCE: 2

```
Met His Leu Leu Ser Leu Leu Ser Ile Ala Thr Leu Ala Val Ala Ser
  1               5                  10                  15

Pro Leu Ser Val Glu Asp Tyr Ala Lys Ala Leu Asp Glu Arg Ala Val
             20                  25                  30

Ser Val Ser Thr Asn Asp Phe Gly Asn Phe Lys Phe Tyr Ile Gln His
         35                  40                  45

Gly Ala Ala Ala Tyr Cys Asn Ser Glu Ala Ala Gly Ala Lys Val
     50                  55                  60

Thr Cys Gly Gly Asn Gly Cys Pro Thr Val Gln Ser Asn Gly Ala Thr
 65                  70                  75                  80

Ile Val Ala Ser Phe Leu Gly Ser Lys Thr Gly Ile Gly Gly Tyr Val
                 85                  90                  95

Ala Thr Asp Ser Ala Arg Lys Glu Ile Val Leu Ser Val Arg Gly Ser
            100                 105                 110

Thr Asn Ile Arg Asn Trp Leu Thr Asn Leu Asp Phe Asp Gln Asp Asp
        115                 120                 125

Cys Ser Leu Thr Ser Gly Cys Gly Val His Gly Gly Phe Gln Arg Ala
    130                 135                 140
```

```
Trp Asn Glu Ile Ser Ala Ala Thr Ala Val Ala Lys Ala Arg
145                 150                 155                 160

Lys Ala Asn Pro Ser Phe Lys Val Val Ala Thr Gly His Ser Leu Gly
            165                 170                 175

Gly Ala Val Ala Thr Leu Ala Gly Ala Asn Leu Arg Val Gly Gly Thr
            180                 185                 190

Pro Val Asp Ile Tyr Thr Tyr Gly Ser Pro Arg Val Gly Asn Thr Gln
            195                 200                 205

Leu Ala Ala Phe Ile Ser Asn Gln Ala Gly Glu Phe Arg Val Thr
        210                 215                 220

Asn Ala Lys Asp Pro Val Pro Arg Leu Pro Pro Leu Val Phe Gly Tyr
225                 230                 235                 240

Arg His Thr Ser Pro Glu Tyr Trp Leu Ser Gly Ser Gly Asn Lys
            245                 250                 255

Val Asp Tyr Thr Ile Asn Asp Val Lys Val Cys Glu Gly Ala Ala Asn
            260                 265                 270

Leu Gln Cys Asn Gly Gly Thr Leu Gly Leu Asp Ile Asp Ala His Leu
        275                 280                 285

His Tyr Phe Gln Glu Thr Asp Ala Cys Ser Gly Ser Gly Ile Ala Trp
        290                 295                 300

Arg Arg Tyr Arg Ser Ala Lys Arg Glu Ser Ile Ser Glu Arg Ala Thr
305                 310                 315                 320

Met Thr Asp Ala Glu Leu Glu Lys Lys Leu Asn Asn Tyr Val Ala Met
            325                 330                 335

Asp Lys Glu Tyr Val Lys Thr His Ala Asn Arg Ser Ser
            340                 345

<210> SEQ ID NO 3
<211> LENGTH: 35
<212> TYPE: DNA
<213> ORGANISM: Fusarium venenatum

<400> SEQUENCE: 3
cagtgaattg gcctcgatgg ccgcggccgc gaatt                               35

<210> SEQ ID NO 4
<211> LENGTH: 35
<212> TYPE: DNA
<213> ORGANISM: Fusarium venenatum

<400> SEQUENCE: 4
aattcgcggc cgcggccatc gaggccaatt cactg                               35

<210> SEQ ID NO 5
<211> LENGTH: 34
<212> TYPE: DNA
<213> ORGANISM: Fusarium venenatum

<400> SEQUENCE: 5
cacgaaggaa agacgatggc tttcacggtg tctg                                34

<210> SEQ ID NO 6
<211> LENGTH: 34
<212> TYPE: DNA
<213> ORGANISM: Fusarium venenatum

<400> SEQUENCE: 6
cagacaccgt gaaagccatc gtctttcctt cgtg                                34
```

-continued

```
<210> SEQ ID NO 7
<211> LENGTH: 46
<212> TYPE: DNA
<213> ORGANISM: Fusarium venenatum

<400> SEQUENCE: 7
ctatctcttc accatggtac cttaattaaa taccttgttg gaagcg                   46

<210> SEQ ID NO 8
<211> LENGTH: 46
<212> TYPE: DNA
<213> ORGANISM: Fusarium venenatum

<400> SEQUENCE: 8
cgcttccaac aaggtattta attaaggtac catggtgaag agatag                   46

<210> SEQ ID NO 9
<211> LENGTH: 37
<212> TYPE: DNA
<213> ORGANISM: Fusarium venenatum

<400> SEQUENCE: 9
cgttctttgt ctgtcagcat gcatctccta tcactcc                             37

<210> SEQ ID NO 10
<211> LENGTH: 45
<212> TYPE: DNA
<213> ORGANISM: Fusarium venenatum

<400> SEQUENCE: 10
ccagagtttt tgttatggtt aattaatatc gttactgcgt aaatg                    45
```

POLYPEPTIDES HAVING LIPASE ACTIVITY AND NUCLEIC ACIDS ENCODING SAME

CROSS-REFERENCE TO RELATED APPLICATION

This application is a divisional of U.S. application Ser. No. 09/703,416 filed on Oct. 31, 2000, now U.S. Pat. No. 6,432,898 which is fully incorporated herein by reference.

BACKGROUND OF THE INVENTION

1. Field of the Invention

The present invention relates to isolated polypeptides having lipase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Lipases (EC 3.1.1.3) are enzymes that can hydrolyze triglycerides to release fatty acid.

Detergents formulated with lipolytic enzymes are known to have improved properties for removing fatty stains. For example, LIPOLASE™ (Novo Nordisk A/S, Bagsvaerd, Denmark), a microbial lipase obtained from the fungus *Thermomyces lanuginosus* (also called *Humicola lanuginosa*), has been introduced into many commercial brands of detergent.

WO 98/26057 discloses a polypeptide having lipase and phospholipase activity (GenBank Acc. No. A85215) obtained from *Fusarium oxysporum*.

It is an object of the present invention to provide improved polypeptides having lipase activity and nucleic acid encoding the polypeptides.

SUMMARY OF THE INVENTION

The present invention relates to isolated polypeptides having lipase activity selected from the group consisting of:

(a) a polypeptide having an amino acid sequence which has at least 85% identity with amino acids 31 to 349 of SEQ ID NO:2;

(b) a polypeptide encoded by a nucleic acid sequence which hybridizes under high stringency conditions with (i) nucleotides 1525 to 2530 of SEQ ID NO:1, (ii) the cDNA sequence contained in nucleotides 1525 to 2530 of SEQ ID NO:1, (iii) a subsequence of (i) or (ii) of at least 100 nucleotides, or (iv) a complementary strand of (i), (ii), or (iii);

(c) a variant of the polypeptide having an amino acid sequence of SEQ ID NO:2 comprising a substitution, deletion, and/or insertion of one or more amino acids; and (d) a fragment of (a) or (b) that has lipase activity.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIGS. 1A and 1B show the genomic DNA sequence and the deduced amino acid sequence of a *Fusarium venenatum* lipase (SEQ ID NOS:1 and 2, respectively).

DETAILED DESCRIPTION OF THE INVENTION

Polypeptides Having Lipase Activity

Figure 2:
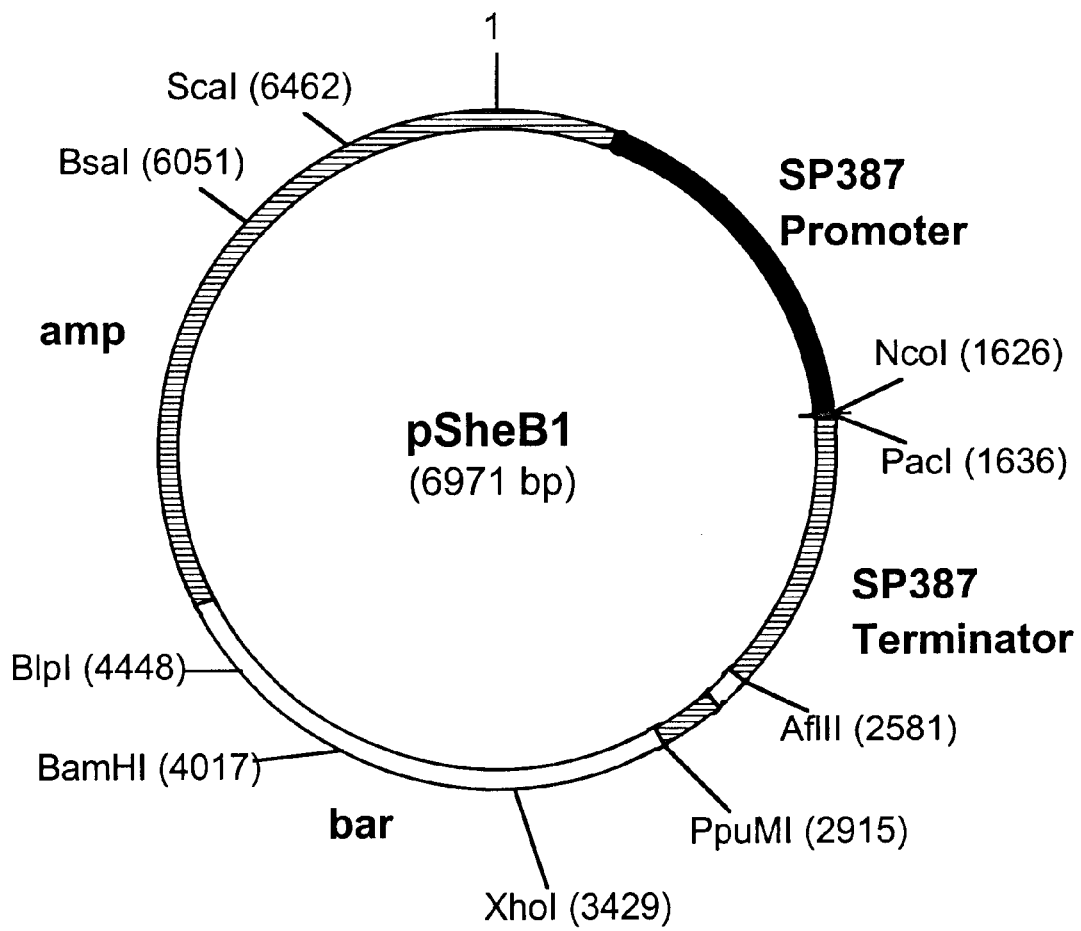
FIG. 2 shows a restriction map of pSheB1.

The term "lipase activity" is defined herein as a triacylglycerol acylhydrolase activity which catalyzes the hydrolysis of a triacylglycerol to diacylglycerol and a fatty acid anion.

A substrate for lipase is prepared by emulsifying tributyrin (glycerin tributyrate) using gum Arabic as emulsifier. The hydrolysis of tributyrin at 30° C. at pH 7 is followed in a pH-stat titration experiment. One unit of lipase activity (1 LU) equals the amount of enzyme capable of releasing 1 $\mu$mol butyric acid/minute at the standard conditions. 1 KLU=1000 LU. For purposes of the present invention, however, lipase activity is determined by measuring the hydrolysis of 2 mM p-nitrophenyl butyrate in 100 mM MOPS pH 7.5, 4 mM CaCl$_2$, 990 $\mu$l of DMSO, 80 $\mu$l of 1% AOS at pH 7.5, 25° C. One unit of lipase activity is defined as 1.0 $\mu$mole of p-nitro phenolate anion produced per minute at 25° C., pH 7.5.

In a first embodiment, the present invention relates to isolated polypeptides having an amino acid sequence which has a degree of identity to amino acids 31 to 349 of SEQ ID NO:2 (i.e., the mature polypeptide) of at least about 85%, preferably at least about 90%, more preferably at least about 95%, and most preferably at least about 97%, which have lipase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 31 to 349 of SEQ ID NO:2. For purposes of the present invention, the degree of identity between two amino acid sequences is determined by the Clustal method (Higgins, 1989, CABIOS 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Preferably, the polypeptides of the present invention comprise the amino acid sequence of SEQ ID NO:2 or an allelic variant thereof; or a fragment thereof that has lipase activity. In a more preferred embodiment, the polypeptide of the present invention comprises the amino acid sequence of SEQ ID NO:2. In another preferred embodiment, the polypeptide of the present invention comprises amino acids 31 to 349 of SEQ ID NO:2, or an allelic variant thereof; or a fragment thereof that has lipase activity. In another preferred embodiment, the polypeptide of the present invention comprises amino acids 31 to 349 of SEQ ID NO:2. In another preferred embodiment, the polypeptide of the present invention consists of the amino acid sequence of SEQ ID NO:2 or an allelic variant thereof; or a fragment thereof that has lipase activity. In another preferred embodiment, the polypeptide of the present invention consists of the amino acid sequence of SEQ ID NO:2. In another preferred embodiment, the polypeptide consists of amino acids 31 to 349 of SEQ ID NO:2 or an allelic variant thereof; or a fragment thereof that has lipase activity. In another preferred embodiment, the polypeptide consists of amino acids 31 to 349 of SEQ ID NO:2.

A fragment of SEQ ID NO:2 is a polypeptide having one or more amino acids deleted from the amino and/or carboxyl terminus of this amino acid sequence. Preferably, a fragment contains at least 260 amino acid residues, more preferably at least 280 amino acid residues, and most preferably at least 300 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated polypeptides having lipase activity which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 1525 to 2530 of SEQ ID NO:1, (ii) the cDNA sequence contained in nucleotides 1525 to 2530 of SEQ ID NO:1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). The subsequence of SEQ ID NO:1 may be at least 100 nucleotides or preferably at least 200 nucleotides. Moreover, the subsequence may encode a polypeptide fragment which has lipase activity. The polypeptides may also be allelic variants or fragments of the polypeptides that have lipase activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having lipase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and, which encodes a polypeptide having lipase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO:1. In another preferred embodiment, the nucleic acid probe is the mature polypeptide coding region of SEQ ID NO:1. In another preferred embodiment, the nucleic acid probe is the nucleic acid sequence contained in plasmid pEJG60 which is contained in *Escherichia coli* NRRL B-30333, wherein the nucleic acid sequence encodes a polypeptide having lipase activity. In another preferred embodiment, the nucleic acid probe is the mature polypeptide coding region contained in plasmid pEJG60 which is contained in *Escherichia coli* NRRL B-30333.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to variants of the polypeptide having an amino acid sequence of SEQ ID NO:2 comprising a substitution, deletion, and/or insertion of one or more amino acids.

The amino acid sequences of the variant polypeptides may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fourth embodiment, the present invention relates to isolated polypeptides having immunochemical identity or partial immunochemical identity to the polypeptide having the amino acid sequence of SEQ ID NO:2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 or the mature polypeptide thereof are prepared by immunizing rabbits (or other rodents) according to the, procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the lipase activity of the mature polypeptide of SEQ ID NO:2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred embodiment, the polypeptide is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* polypeptide.

In a more preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium*

*venenatum* regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, taxonomic equivalents of Fusarium are defined by D. L. Hawksworth, P. M. Kirk, B. C. Sutton, and D. N. Pegler (editors), 1995, In Ainsworth & Bisby's *Dictionary of the Fungi*, Eighth Edition, CAB International, University Press, Cambridge, England, pp.173–174.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-lipase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO:1. In another more preferred embodiment, the nucleic acid sequence is the sequence contained in plasmid pEJG60 that is contained in *Escherichia coli* NRRL B-30333. In another preferred embodiment, the nucleic acid sequence is the mature polypeptide coding region of SEQ ID NO:1. In another more preferred embodiment, the nucleic acid sequence is the mature polypeptide coding region contained in plasmid pEJG60 that is contained in *Escherichia coli* NRRL B-30333. The present invention also encompasses nucleic acid sequences which encode a polypeptide having the amino acid sequence of SEQ ID NO:2 or the mature polypeptide thereof, which differ from SEQ ID NO:1 by virtue of the degeneracy of the genetic code. The present invention also relates to subsequences of SEQ ID NO:1 which encode fragments of SEQ ID NO:2 that have lipase activity.

A subsequence of SEQ ID NO:1 is a nucleic acid sequence encompassed by SEQ ID NO:1 except that one or more nucleotides from the 5' and/or 3' end have been deleted. Preferably, a subsequence contains at least 780 nucleotides, more preferably at least 840 nucleotides, and most preferably at least 900 nucleotides. The present invention also relates to mutant nucleic acid sequences comprising at least one mutation in the mature polypeptide coding sequence of SEQ ID NO:1, in which the mutant nucleic acid sequence encodes a polypeptide which consists of amino acids 31 to 349 of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Fusarium, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO:1 (i.e., nucleotides 1525 to 2530) of at least about 85%, preferably about 90%, more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for lipase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO:1 or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 1525 to 2530 of SEQ ID NO:1, (ii) the cDNA sequence contained in nucleotides 1525 to 2530 of SEQ ID NO:1, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has lipase activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO:1 or a subsequence thereof, wherein the mutant nucleic acid sequence encodes a polypeptide which consists of amino acids 31 to 349 of SEQ ID NO:2 or a fragment thereof which has lipase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xyIA and xyIB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred embodiment, the signal peptide coding region is nucleotides 1376 to 1420 of SEQ ID NO:1 which encode amino acids 1 to 15 of SEQ ID NO:2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

In a preferred embodiment, the propeptide coding region is nucleotides 1421 to 1465 of SEQ ID NO:1 which encode amino acids 16 to 30 of SEQ ID NO:2.

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid, sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of, which provides for biocide or viral resistance, resistance to heavy metals, prototrophy to auxotrophs, and the like. Examples of bacterial selectable markers are the dal genes from Bacillus subtilis or Bacillus licheniformis, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are the amdS and pyrG genes of Aspergillus nidulans or Aspergillus oryzae and the bar gene of Streptomyces hygroscopicus.

The vectors of the present invention preferably contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in E. coli, and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, Proceedings of the National Academy of Sciences USA 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* and *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus*, or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce the polypeptide; and (b) recovering the polypeptide. Preferably, the strain is of the genus Fusarium, and more preferably *Fusarium venenatum*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO:1, wherein the mutant nucleic acid sequence encodes a polypeptide which consists of amino acids 31 to 349 of SEQ ID NO:2, and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having lipase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and Theological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a Vicia faba promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al.,1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having lipase activity of the present invention under conditions conducive for production of the polypeptide; and (b) recovering the polypeptide.

Removal or Reduction of Lipase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell when cultivated under the same conditions.

The construction of strains which have reduced lipase activity may be conveniently accomplished by modification or inactivation of a nucleic acid sequence necessary for expression of the polypeptide having lipase activity in the cell. The nucleic acid sequence to be modified or inactivated may be, for example, a nucleic acid sequence encoding the polypeptide or a part thereof essential for exhibiting lipase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the lipase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced lipase activity or production.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell of choice is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of lipase activity by fermentation of a cell which produces both a polypeptide of the present invention as well as the protein product of interest by adding an effective amount of an agent capable of inhibiting lipase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of lipase activity by cultivating the cell under conditions permitting the expression of the product, subjecting the resultant culture broth to a combined pH and temperature treatment so as to reduce the lipase activity substantially, and recovering the product from the culture broth. Alternatively, the combined pH and temperature treatment may be performed on an enzyme preparation recovered from the culture broth. The combined pH and temperature treatment may optionally be used in combination with a treatment with a lipase inhibitor.

In accordance with this aspect of the invention, it is possible to remove at least 60%, preferably at least 75%, more preferably at least 85%, still more preferably at least 95%, and most preferably at least 99% of the lipase activity. Complete removal of lipase activity may be obtained by use of this method.

The combined pH and temperature treatment is preferably carried out at a pH in the range of 6.5–7 and a temperature in the range of 25–40° C. for a sufficient period of time to attain the desired effect, where typically, 30 to 60 minutes is sufficient.

The methods used for cultivation and purification of the product of interest may be performed by methods known in the art.

The methods of the present invention for producing an essentially lipase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The lipase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from lipase activity which is produced by a method of the present invention.

Compositions

In a still further aspect, the present invention relates to compositions comprising a polypeptide of the present invention. Preferably, the compositions are enriched in a polypeptide of the present invention. In the present context, the term "enriched" indicates that the lipase activity of the composition has been increased, e.g., with an enrichment factor of 1.1.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus Aspergillus, preferably *Aspergillus aculeatus, Aspergillus awamori, Aspergillus niger*, or *Aspergillus oryzae*, or Trichoderma, Humicola, preferably *Humicola insolens*, or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having lipase activity in any industrial application of lipases, e.g., in detergents.

Use in Detergent

The variant may be used as a detergent additive, e.g., at a concentration (expressed as pure enzyme protein) of 0.001–10 (e.g., 0.01–1) mg per gram of detergent or 0.001–100 (e.g. 0.01–10) mg per liter of wash liquor.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations. In a laundry detergent, the variant may be effective for the removal of fatty stains, for whiteness maintenance and for dingy cleanup. A laundry detergent composition may be formulated as described in WO 97/04079, WO 97/07202, WO 97/41212, PCT/DK WO 98/08939 and WO 97/43375.

The detergent composition of the invention may particularly be formulated for hand or machine dishwashing operations e.g., as described in GB 2,247,025 (Unilever) or WO 99/01531 (Procter & Gamble). In a dishwashing composition, the variant may be effective for removal of greasy/oily stains, for prevention of the staining/discoloration of the dishware and plastic components of the dishwasher by highly colored components and the avoidance of lime soap deposits on the dishware.

Use in Degumming

A polypeptide of the present invention may be used for degumming an aqueous carbohydrate solution or slurry to improve its filterability, particularly, a starch hydrolysate, especially a wheat starch hydrolysate which is difficult to filter and yields cloudy filtrates. The treatment may be performed using methods well known in the art. See, for example, EP 219,269 and EP 808,903.

Signal Peptide and Propeptide

The present invention also relates to nucleic acid constructs comprising a gene encoding a protein operably linked to one or both of a first nucleic acid sequence consisting of nucleotides 1376 to 1429 of SEQ ID NO:1 encoding a signal peptide consisting of amino acids 1 to 15 of SEQ ID NO:2 and a second nucleic acid sequence consisting of nucleotides 1421 to 1465 of SEQ ID NO:1 encoding a propeptide consisting of amino acids 16 to 30 of SEQ ID NO:2, wherein the gene is foreign to the first and second nucleic acid sequences.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The first and second nucleic acid sequences may be operably linked to foreign genes individually with other control sequences or in combination with other control sequences. Such other control sequences are described supra. As noted earlier, where both signal peptide-and propeptide regions are present at the amino terminus of a protein, the propeptide region is positioned next to the amino terminus of a protein and the signal peptide region is positioned next to the amino terminus of the propeptide region.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Chemicals used as buffers and substrates were commercial products of at least reagent grade.

Strains

*Fusarium venenatum* WTY700 3.8d, a spore-purified tri5-minus, dps1-minus strain, was used as the recipient strain for transformation experiments. *Fusarium venenatum* WTY700 3.8d is a morphological mutant of *Fusarium venenatum* strain ATCC 20334 (Wiebe et al., 1991, *Mycol. Research* 95: 1284–1288),

Example 1

Fermentation and Mycelial Tissue

*Fusarium venenatum* WTY700 3.8d was grown in a two-liter lab-scale fermentor using a fed-batch fermentation scheme with NUTRIOSE™ (Roquette Freres, S. A., Beinheim, France) as the carbon source and yeast extract. Ammonium phosphate was provided in the feed. The fermentation was maintained at pH 6–6.5 and 30 ° C. with positive dissolved oxygen.

Mycelial samples were harvested at 2, 4, 6, and 8 days post-inoculum and quick-frozen in liquid nitrogen. The samples were stored at −80° C. until they were disrupted for RNA extraction.

Example 2 cDNA Library Construction

Total cellular RNA was extracted from the mycelial samples described in Example 1 according to the method of Timberlake and Barnard (1981, *Cell* 26: 29–37), and the RNA samples were analyzed by Northern hybridization after blotting from 1% formaldehyde-agarose gels (Davis et al., 1986, *Basic Methods in Molecular Biology*, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized, using approximately 5 μg of poly(A)+mRNA according to the method of Gubler and Hoffman (1983, *Gene* 25: 263–269) except a NotI-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

The cDNA was digested with NotI, size selected by agarose gel electrophoresis (ca. 0.7–4.5 kb), and ligated with pZErO-2.1 (Invitrogen Corporation, Carlsbad, Calif.) which had been cleaved with NotI plus EcoRV and dephosphorylated with calf-intestine alkaline phosphatase (Boehringer Mannheim Corporation, Indianapolis, Ind.). The ligation mixture was used to transform competent E. coli TOP10 cells (Invitrogen Corporation, Carlsbad, Calif.). Transformants were selected on 2YT agar plates (Miller, 1992, *A Short Course in Bacterial Genetics. A Laboratory Manual and Handbook for Escherichia coli and Related Bacteria*, Cold Spring Harbor Press, Cold Spring Harbor, N.Y.) which contained kanamycin at a final concentration of 50 µg/ml.

Example 3
Template Preparation and Nucleotide Sequencing

From the cDNA library described in Example 2, 1192 transformant colonies were picked directly from the transformation plates into 96-well microtiter dishes which contained 200 µl of 2YT broth (Miller, 1992, supra) with 50 µg/ml kanamycin. The plates were incubated overnight at 37° C. without shaking. After incubation 100 µl of sterile 50% glycerol was added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 µg of kanamycin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using the 96-well Miniprep Kit protocol of Advanced Genetic Technologies Corporation (Gaithersburg, Md.) as modified by Utterback et al. (1995, *Genome Sci. Technol.* 1: 1–8). Single-pass DNA sequencing (EST) was done with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47–60) and the reverse lac sequencing primer.

Example 4
Analysis of DNA Sequence Data

Nucleotide sequence data were scrutinized for quality, and samples giving improper spacing or ambiguity levels exceeding 3% were discarded or re-run. Vector sequences and ambiguous base calls at the ends of the DNA sequences were trimmed with assistance of FACTURA™ software (Perkin-Elmer Applied Biosystems, Inc., Foster City, Calif. All sequences were compared to each other to determine multiplicity using AutoAssembler™ software (Perkin-Elmer Applied Biosystems, Inc., Foster City, Calif.). Lastly, all sequences were translated in three frames and searched against a non-redundant database (NRDB) using GeneAssist™ software (Perkin-Elmer Applied Biosystems, Inc., Foster City, Calif.) with a modified Smith-Waterman algorithm using the BLOSUM 62 matrix with a threshold score of 70. The NRDB was assembled from Genpept, Swiss-Prot, and PIR databases.

Example 5
Identification of Lipase 1 cDNA Clones

Putative lipase clones were identified by comparing the deduced amino acid sequence of the ESTs to protein sequences deposited in publicly available databases such as Swissprot, Genpept, and PIR using a modified Smith-Waterman search algorithm (Perkin-Elmer Applied Biosystems, Foster City, Calif.). Tentative identification was based on amino acid sequence similarity to numerous fungal lipases. One clone, *Fusarium venenatum* EST FA0726, was selected for nucleotide sequence analysis which revealed that the cDNA clone was truncated at its 5 prime end.

Example 6
Fusarium Venenatum Genomic DNA Extraction

*Fusarium venenatum* WTY700 was grown for 24 hours at 28° C. and 150 rpm in 25 ml of YEG medium composed per liter of 5 g of yeast extract and 20 g of glucose. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to ensure mixing, and extracted twice with an equal volume of phenol:chloroform:isoamyl alcohol (25:24:1 v/v/v). Sodium acetate (3 M solution) was added to give a final concentration of 0.3 M and the nucleic acids were precipitated with 2.5 volumes of ice cold ethanol. The tube was centrifuged at 15,000×g for 30 minutes and the pellet was allowed to air dry for 30 minutes before resuspension in 0.5 ml of TE buffer. DNase-free ribonuclease A was added to a concentration of 100 µg/ml and the mixture was incubated at 37° C. for 30 minutes. Proteinase K (200 µg/ml) was then added and the mixture was incubated an additional hour at 37° C. Finally, the mixture was extracted twice with phenol:chloroform:isoamyl alcohol (25:24:1 v/v/v) before precipitating the DNA with sodium acetate and ethanol according to standard procedures. The DNA pellet was dried under vacuum, resuspended in TE buffer, and stored at 4° C.

Example 7
Genomic DNA Library Construction, Screening, and Isolation of Genomic Lipase 1 Clone Genomic libraries of *Fusarium venenatum* WTY700 were constructed in λZipLox according to the manufacturer's instructions (Life Technologies, Gaithersburg, Md.). *Fusarium venenatum* genomic DNA was partially digested with Tsp509I and size-fractionated on 1% agarose gels. DNA fragments migrating in the size range 3–7 kb were excised and eluted from the agarose gel slices using Prep-a-Gene reagents (BioRad, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *E. coli* Y1090ZL cells.

The cDNA from *Fusarium venenatum* clone FA0726 was excised from the vector plasmid by digestion with EcoRI and NotI yielding an approximately 900 bp fragment. The fragment was purified by gel electrophoresis, and radiolabeled with $\alpha[^{32}P]$ dCTP using a Prime-it Random Primer Labeling Kit (Stratagene, La Jolla, Calif.).

Approximately 40,000 plaques from the library were screened by plaque-hybridization (Davis et al., 1980, supra)

with the radiolabeled probe fragment of the *Fusarium venenatum* lipase gene using high stringency conditions at 45° C. (high stringency=50% formamide, 5×SSPE, 0.3% SDS, 200 µg/ml sheared and denatured salmon sperm DNA). Plaques, which gave hybridization signals, were purified once in *E. coli* DH10B cells, and the individual clones were subsequently excised from the λZipLox vector as pZL1-derivatives (D'Alessio et al., 1992, Focus® 14: 7).

One plaque was identified that hybridized strongly to the *Fusarium venenatum* lipase gene probe, and was subsequently excised from the λZipLox vector as a pZL1-derivative (D'Alessio et al., 1992, supra). Plasmid DNA was isolated from the clone by passage through *E. coli* DH10B cells (Life Technologies, Gaithersburg, Md.) according to the manufacturer's instructions. This clone was designated *E. coli* DH10B-pFvLipase1.

Example 8
Characterization of the *Fusarium Venenatum* Genomic Clone Encoding Lipase 1

DNA sequencing was performed on an Perkin-Elmer Biosystems Model 377 XL Automated DNA Sequencer using dye-terminator chemistry (Giesecke et al., 1992, *Journal of Virology Methods* 38: 47–60). Contig sequences were generated using a transposon insertion strategy (Primer Island Transposition Kit, Perkin-Elmer/Applied Biosystems, Inc., Foster City, Calif.). The 2.94 kb genomic fragment was sequenced to an average redundancy of 4.8.

Figure 1A:
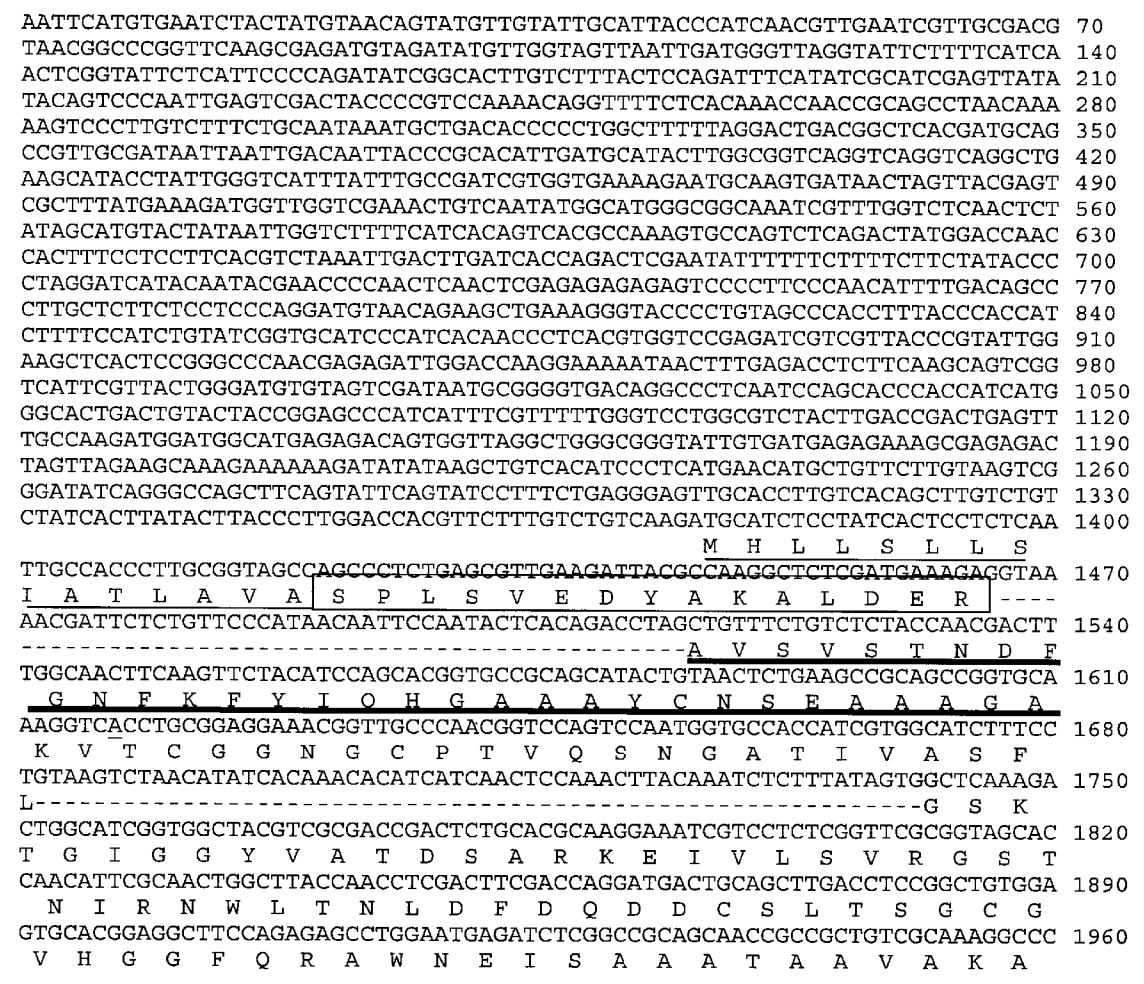

The nucleotide sequence and deduced amino acid sequence are shown in FIG. 1. The insert contains an open reading frame of 1.153 kb encoding a polypeptide of 350 amino acids. Using the SignalP software program (Nielsen et al., 1997, *Protein Engineering* 10: 1–6), a signal peptide of 15 residues was predicted. The predicted signal peptide is followed by a 15 residue propeptide ending with a concanical propeptide Glu/Arg cleavage site. N-terminal sequencing of the lipase 1 protein supports this propeptide cleavage site prediction. The open reading frame is interrupted by two introns of 49 bp and 58 bp. Thus, the mature *Fusarium venenatum* lipase comprises 319 amino acids and a predicted molecular weight of 33.6 kDa. There are 2 potential N-linked glycosylation sites (Asn-X-Ser/Thr) within *Fusarium venenatum* lipase 1.

A comparative alignment of lipase sequences using the Clustal W algorithm in the Megalign program of DNA-Star, showed that the deduced amino acid sequence of the *Fusarium venenatum* lipase 1 gene shares 81% identity to the deduced amino acid sequence of a *Fusarium oxysporum* phospholipase A (EP0869167).

Example 9

Construction of Plasmid pSheB1

The *Fusarium venenatum* expression vector pSheB1 (FIG. 2) was generated by modification of pDM181 (WO 98/20136). The modifications included (a) removal of two NcoI sites within the pDM181 sequence, and (b) restoration of the natural translation start of the *Fusarium oxysporum* trypsin promoter (reconstruction of an NcoI site at the ATG start codon).

Removal of two NcoI sites within the pDM181 sequence was accomplished using the QuikChange™ site-directed mutagenesis kit (Stratagene Cloning Systems, La Jolla, Calif.) according to the manufacturer's instruction with the following pairs of mutagenesis primers:

```
5'-dCAGTGAATTGGCCTCGATGGCCGCGGCCGCGAATT-3'  plus  (SEQ ID NO:3)

5'-dAATTCGCGGCCGCGGCCATCGAGGCCAATTCACTG-3'        (SEQ ID NO:4)

5'-dCACGAAGGAAAGACGATGGCTTTCACGGTGTCTG-3'   plus  (SEQ ID NO:5)

5'-dCAGACACCGTGAAAGCCATCGTCTTTCCTTCGTG-3'         (SEQ ID NO:6)
```

Restoration of the natural translation start of the *Fusarium oxysporum* trypsin promoter was also accomplished using the Stratagene QuikChange™ site directed mutagenesis kit in conjunction with the following pair of mutagenesis primers:

```
5'-dCTATCTCTTCACCATGGTACCTTAATTAAATACCTTGTTGGAAGCG-3'  plus  (SEQ ID NO:7)

5'-dCGCTTCCAACAAGGTATTTAATTAAGGTACCATGGTGAAGAGATAG-3'        (SEQ ID NO:8)
```

All site-directed changes were confirmed by DNA sequence analysis of the appropriate vector regions.

Example 10
Construction of Expression Vector pEJG60

The lipase-expression vector, pEJG60 was constructed as follows. The lipase coding region was amplified from pFv-lipase1 using the following pair of primers:

```
Primer 990658:

5'-CGTTCTTTGTCTGTCAGCATGCATCTCCTATCACTCC-3'       (SEQ ID NO:9)

Primer 990661:

5'-CCAGAGTTTTTGTTATGGTTAATTAATATCGTTACTGCGTAAATG-3'  (SEQ ID NO:10)
```

The forward primer introduces a SphI site which contains the ATG, and the reverse primer introduces a PacI site after the stop codon.

The amplification reaction (100 μl) contained the following components: 0.5 μg of genomic clone, pFvLipase1, 50 pmol of the forward primer, 50 pmol of the reverse primer, 10 mM dNTPs (dATP, dCTP, dGTP, and dTTP), 1×Pwo DNA polymerase buffer, and 2.5 units of Pwo DNA polymerase (Boehringer Mannheim, Indianapolis, Ind.). The reactions were incubated in a Perkin-Elmer Model 480 Thermal Cycler programmed for 1 cycles at 95° C. for 2 minutes; 10 cycles at 94° C. for 45 seconds, 55° C. for 45 seconds, and 72° C. for 2 minutes; 17 cycles at 94° C. for 45 seconds, 55° C. for 45 seconds, and 72° C. for 2 minutes with an extension of 20 seconds per cycle; 1 cycle at 72° C. for 10 minutes; and a soak cycle at 4° C. The reaction products were isolated on a 1% agarose gel where a 1.15 kb product band was excised from the gel and purified using Qiaquik Gel Extraction Kit (Qiagen, Chatsworth, Calif.) according to the manufacturer's instructions.

Figure 3:
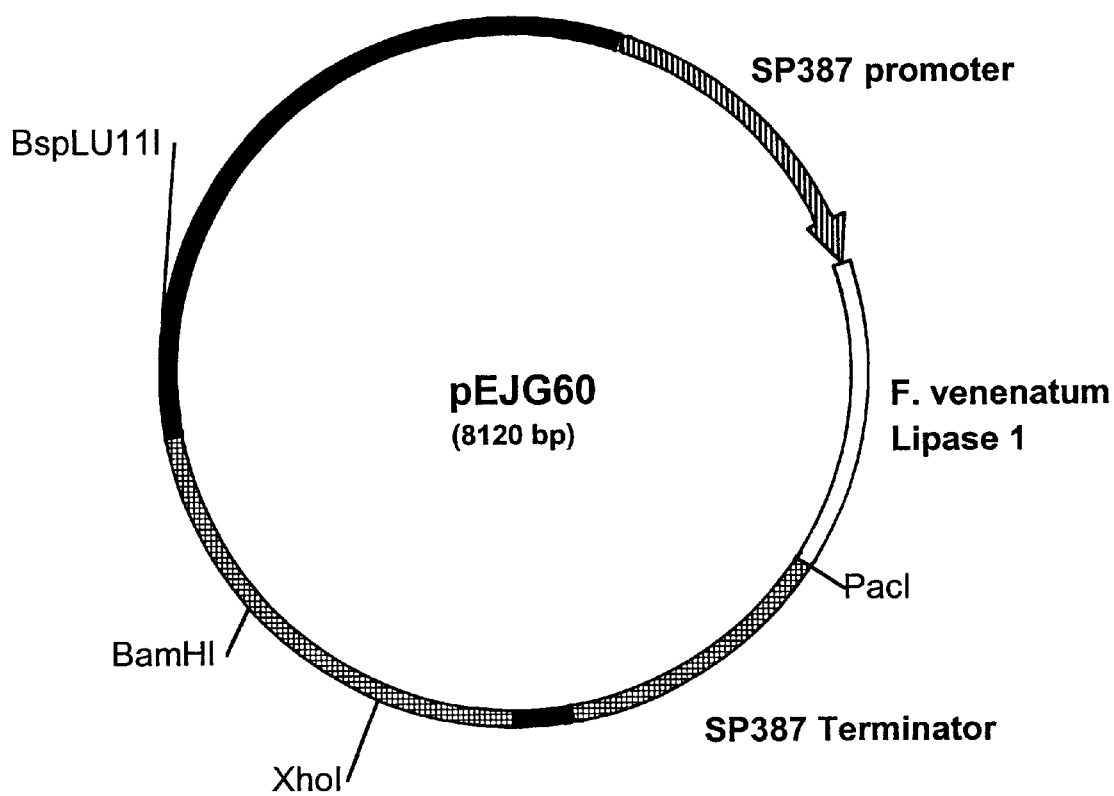
FIG. 3 show a restriction map of pEJG60.

The generated fragment was digested with SphI, blunted with Klenow, digested with PacI, and purified by agarose gel electrophoresis and Qiaquik Gel Extraction Kit (Qiagen, Chatsworth, Calif.). The purified DNA segment was ligated into pSheB1 (FIG. 2) which was previously NcoI digested, treated with DNA polymerase I (Klenow fragment), and digested with PacI. The treatment of the NcoI-digested vector with Klenow fragment resulted in a filling in of the NcoI cohesive end, thereby making it blunt and compatible with the blunt site of the lipase DNA segment. The resulting expression plasmid was designated pEJG60 (FIG. 3). The PCR-amplified lipase gene segment was re-sequenced to verify the absence of any errors.

Example 10
Transformation of *Fusarium Venenatum* and Analysis of *Fusarium Venenatum* Transformants Spores of *Fusarium venenatum* WTY700 were generated by inoculating a flask containing 500 ml of RA sporulation medium with 10 plugs from a 1×Vogels medium plate (2.5% Noble agar) supplemented with 2.5% glucose and 2.5 mM sodium nitrate and incubating at 28° C., 150 rpm for 2 to 3 days. Spores were harvested through Miracloth (Calbiochem, San Diego, Calif.) and centrifuged 20 minutes at 7000 rpm in a Sorvall RC-5B centrifuge (E. I. DuPont De Nemours and Co., Wilmington, Del.). Pelleted spores were washed twice with sterile distilled water, resuspended in a small volume of water, and then counted using a hemocytometer.

Protoplasts were prepared by inoculating 100 ml of YEPG medium with $4 \times 10^7$ spores of *Fusarium venenatum* WTY700 and incubating for 16 hours at 24° C. and 150 rpm. The culture was centrifuged for 7 minutes at 3500 rpm in a Sorvall RT 6000D (E. I. DuPont De Nemours and Co., Wilmington, Del.). Pellets were washed twice with 30 ml of 1 M $MgSO_4$ and resuspended in 15 ml of 5 mg/ml of NOVOZYME 234™ (batch PPM 4356, Novo Nordisk A/S, Bagsvaerd, Denmark) in 1 M $MgSO_4$. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC:SPTC:DMSO to a final concentration of $1.25 \times 10^7$ protoplasts/ml. The protoplasts were stored at −80° C., after controlled-rate freezing in a Nalgene Cryo 1° C. Freezing Container (VWR Scientific, Inc., San Francisco, Calif.).

Frozen protoplasts of Fusarium venenatum WTY700 were thawed on ice. Five μg of pEJG60 described in Example 10 and 5 μl of heparin (5 mg per ml of STC) was added to a 50 ml sterile polypropylene tube. One hundred μl of protoplasts was added, mixed gently, and incubated on ice for 30 minutes. One ml of SPTC was added and incubated 20 minutes at room temperature. After the addition of 25 ml of 40° C. COVE top agarose, the mixture was poured onto an empty 150 mm diameter plate and incubated overnight at room temperature. Then an additional 25 ml of 40° C. COVE top agarose containing 10 mg of BASTA™ per ml was poured on top of the plate and incubated at room temperature for up to 14 days. The active ingredient in the herbicide BASTA™ is phosphinothricin. BASTA™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use.

Twenty-four transformants were picked directly from the selection plates (COVE underlay with COVE-BASTA™ overlay) and inoculated into 125 ml shake flasks containing 25 ml of M400Da medium supplemented with 1 mM $CaCl_2$ and 100 μg/ml ampicillin (to prevent bacterial contamination) and incubated at 28° C., 200 rpm on a platform shaker for 7 days. The untransformed recipient strain was also included as a negative control.

Flasks were sampled at 5 and 7 days and assayed for lipase activity as described below. The samples were also submitted to SDS-PAGE using Novex gradient gels (Novex Experimental Technology, San Diego, Calif.).

Lipase activity was determined as follows: 100 μl of substrate (3.92 ml of 100 mM MOPS pH 7.5, 4 mM $CaCl_2$, 990 μl of DMSO, 80 μl of 1% AOS, and 20 μl of p-nitrophenyl butyrate) was added to 100 μl of diluted sample. The samples were diluted accordingly in 100 mM MOPS pH 7.5, 4 mM $CaCl_2$. The absorbance at 405 nm was monitored for 3 minutes at room temperature in a 96-well microtiter plate using a Molecular Devices Thermomax Microplate Reader.

The lipase assay results indicated that at both 5 and 7 days, most of the transformants produced lipase activity well above that of the untransformed control. Shake flask culture broths from transformants #1 and #3, the two highest scorers in the lipase assay, were analyzed on a 16% tricine gel. A prominent polypeptide at a apparent molecular weight of 32–33 kD was observed at both time points and for each transformant harboring pEJG60.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| E. coli pEJG60 | NRRL B-30333 | August 22, 2000 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated nucleic acid sequence encoding a polypeptide having lipase activity, selected from the group consisting of:
   (a) a nucleic acid sequence encoding a polypeptide having an amino acid sequence which has at least 90% identity with amino acids 31 to 349 of SEQ ID NO:2;
   (b) a nucleic acid sequence having at least 90% homology with nucleotides 1525 to 2530 of SEQ ID NO:1;
   (c) a nucleic acid sequence which hybridizes under high stringency conditions with (i) nucleotides 1525 to 2530 of SEQ ID NO:1, (ii) the cDNA sequence contained in nucleotides 1525 to 2530 of SEQ ID NO:1, or (iii) a full complementary strand of (i) or (ii); and
   (c) a subsequence of (a), (b), or (c), encoding a polypeptide fragment that has lipase activity.

2. The nucleic acid sequence of claim 1, which encodes polypeptide having an amino acid sequence which has at least 90% identity with amino acids 31 to 349 of SEQ ID NO:2.

3. The nucleic acid sequence of claim 1, which encodes a polypeptide comprising the amino acid sequence of SEQ ID NO:2.

4. The nucleic acid sequence of claim 3, which encodes a polypeptide comprising the amino acids 31 to 349 of SEQ ID NO:2.

5. The nucleic acid sequence of claim 1, which encodes a polypeptide consisting of the amino acid sequence of SEQ ID NO:2 or a fragment thereof which has lipase activity.

6. The nucleic acid sequence of claim 5, which encodes a polypeptide consisting of the amino acid sequence of SEQ ID NO:2.

7. The nucleic acid sequence of claim 6, which encodes a polypeptide consisting of amino acids 31 to 349 of SEQ ID NO:2.

8. The nucleic acid sequence of claim 1, which has at least 90% homology with nucleotides 1525 to 2530 of SEQ ID NO:1.

9. The nucleic acid sequence of claim 1, which hybridizes under high stringency conditions with (i) nucleotides 1525 to 2530 of SEQ ID NO:1, (ii) the cDNA sequence contained in nucleotides 1525 to 2530 of SEQ ID NO:1, or (iii) a full complementary strand of (i) or (ii).

10. The nucleic acid sequence of claim 1, which has the nucleic acid sequence of SEQ ID NO:1.

11. The nucleic acid sequence of claim 1, which is contained in plasmid pEJG60 which is contained in *E. coil* NRRL B-30333.

12. A nucleic acid construct comprising the nucleic acid sequence of claim 1 operably linked to one or more control sequences which direct the production of the polypeptide in a suitable expression host.

13. A recombinant expression vector comprising the nucleic acid construct of claim 12, a promoter, and transcriptional and translational stop signals.

14. A recombinant host cell comprising the nucleic acid construct of claim 12.

15. A method for producing a polypeptide having lipase activity comprising (a) cultivating the host cell of claim 14 under conditions suitable for production of the polypeptide; and (b) recovering the polypeptide.

* * * * *